United States Patent [19]

Eberl

[11] 4,258,442
[45] Mar. 31, 1981

[54] BREAST PROSTHESIS WITH STIFFENING RIBS

[76] Inventor: Tertulin Eberl, Konigsdorfer Strasse 35, D-8170 Bad Tolz, Fed. Rep. of Germany

[21] Appl. No.: 31,199

[22] Filed: Apr. 18, 1979

[30] Foreign Application Priority Data

Apr. 28, 1978 [DE] Fed. Rep. of Germany ... 7813097[U]
May 10, 1978 [DE] Fed. Rep. of Germany ... 7814123[U]

[51] Int. Cl.³ .................................................. A61F 1/00
[52] U.S. Cl. ............................................ 3/36; 128/465
[58] Field of Search ....................... 3/36; 128/463, 465

[56] References Cited

U.S. PATENT DOCUMENTS

| 146,805 | 1/1874 | Cox | 3/36 X |
| 401,028 | 4/1889 | Greene | 3/36 X |
| 2,611,898 | 9/1952 | Laird | 128/463 |

FOREIGN PATENT DOCUMENTS

| 2457041 | 6/1976 | Fed. Rep. of Germany | 3/36 |
| 2605148 | 8/1977 | Fed. Rep. of Germany | 3/36 |

Primary Examiner—Clifford D. Crowder
Attorney, Agent, or Firm—Zarley, McKee, Thomte, Voorhees & Sease

[57] ABSTRACT

The invention relates to a breast prosthesis consisting of an elastic material with a convex outer surface connected by means of an annular rim surface facing the body to a concave inside surface, stiffening ribs being provided on the concave inside surface which are radial with respect to the center.

4 Claims, 6 Drawing Figures

BREAST PROSTHESIS WITH STIFFENING RIBS

BACKGROUND OF THE INVENTION

A breast prosthesis of this kind is known for instance from the German Gebrauchsmuster 1 739 612. The elastic materials presently used for breast prosthesises are of approximately the same density as the human flesh. Nevertheless it has been found that such breast prosthesises are too heavy to give the bearer the feeling of a balanced weight. Furthermore there is frequently chafing of the breast scar. Therefore breast prosthesises have been provided with a cavity on the side facing the body. This lightens the weight of the prosthesis and reduces chafing. However this also creates a new problem, namely that it is easy to compress the prosthesis. To stiffen such prosthesises, the cited German Gebrauchsmuster 1 739 612 provides stiffening ribs on the concave inside surface which are radial with respect to the center.

Thereby however the cavity is subdivided into several chambers and it has been observed that even following slight compression, for instance when dancing, the breast prosthesis together with at least a few clamps is sucked against the body. As regards breast prosthesises lacking stiffening ribs in the cavity, there is less danger of this happening because the rim of the breast prosthesis deforms more easily and therefore air can get into this cavity.

SUMMARY OF THE INVENTION

It is one object of the invention therefore to further develop a breast prosthesis of the initially discussed kind, for which the danger of suction is eliminated or at least extensively reduced.

The invention solves this problem in that the stiffening ribs terminate before reaching the center and/or in that at least some of them project beyond the rim surface or are recessed with respect to it.

The term stiffening ribs in the sense of the present invention covers all lengthwise bosses or elevations extending over a substantial part of the concave inside surface of the breast prosthesis.

As regards the embodiments for which the stiffening ribs pointing radially toward the center and terminating before reaching it and/or being recessed from the rim surface, only a single chamber is present underneath the breast prosthesis, said chamber being less stiff than if the stiffening ribs went all the way to the center and would reach the level of the rim surfaces, whereby several chambers would be formed. The peripheral rim of the breast prosthesis accordingly does everywhere tightly touch the body of the wearer, and accordingly the air can again enter the chamber following a compression of the prosthesis, which will then rise again.

As regards the embodiment comprising projections extending beyond the rim surface, there will always be the tendency of slightly lifting the breast prosthesis from the body, whereby air can reach underneath the prosthesis following its compression, and the prosthesis may lift again without there being suction.

Obviously it is also possible to let the stiffening ribs projecting beyond the rim surface terminate before they reach the center.

The breast prosthesis of the invention consist preferably of silicone rubber known per se, and it may be surrounded—again in manner known per se—by an elastic plastic sheet, especially a foil of polyurethane (not shown).

The basic concept of the present invention can be applied to breast prosthesis of all kinds. Included in particular are round breast prosthesises, furthermore prosthesises with a side flap to compensate for amputations reaching as far as the region of the arm can be adapted to this invention.

BRIEF DESCRIPTION OF THE DRAWINGS

The invention is discussed below in further detail in relation to the attached drawings.

Figure 2:
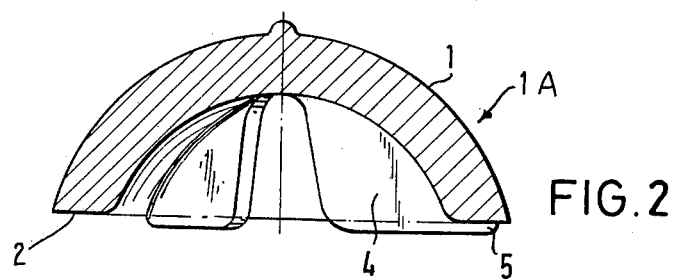
FIG. 2 is a sectional view of the invention taken along line II—II of FIG. 1.
Figure 1:
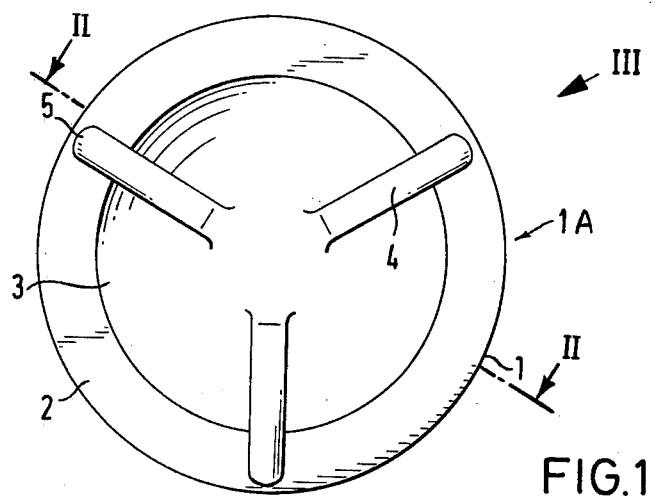
FIG. 1 is a lower view of a breast prosthesis of the invention.
Figure 3:
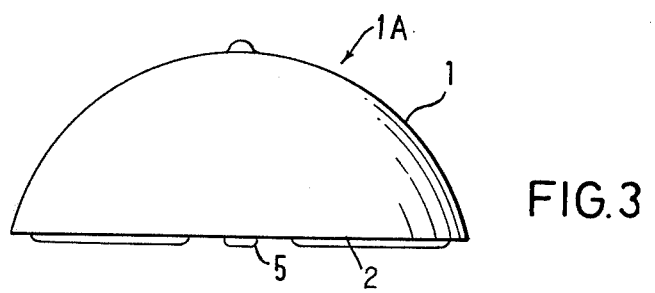
FIG. 3 is a side view of the breast prosthesis of FIG. 1.

The breast prosthesises of FIGS. 1-3 comprises a cup 1A having an outer convex surface 1 and a concave inner surface 3 connected by an annular rim surface 2 facing the body of the wearer. Three stiffening ribs 4 project from the concave inner surface. The stiffening ribs 4 are provided with extensions 5 projecting beyond the rim surface 2. The stiffening ribs 4 terminate before reaching the center of a cavity formed by the concave inside surface 3, so that this cavity is not subdivided into several chambers.

Figure 5:
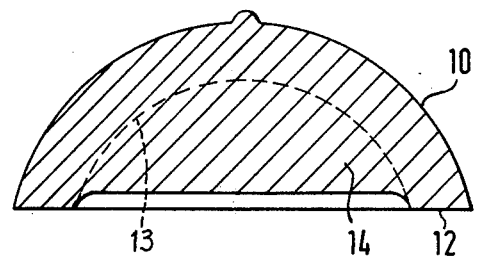
FIG. 5 is a sectional view taken along line V—V of FIG. 4.
Figure 4:
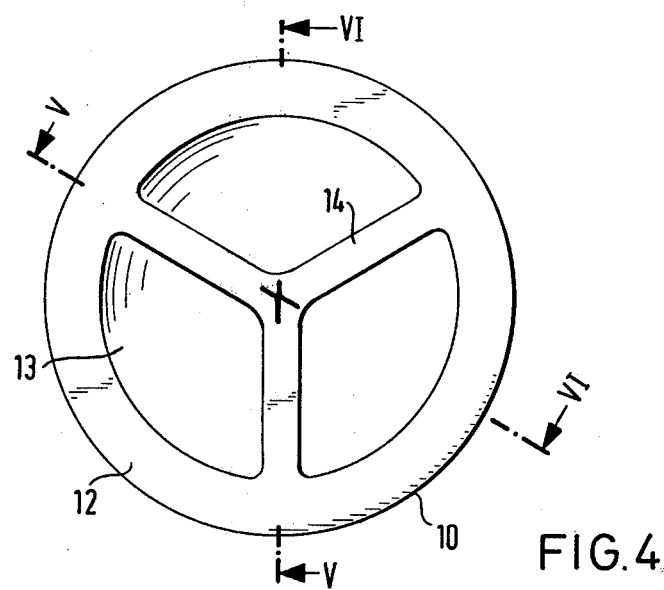
FIG. 4 is a sectional view similar to FIG. 2 of an alternate form of the invention.
Figure 6:
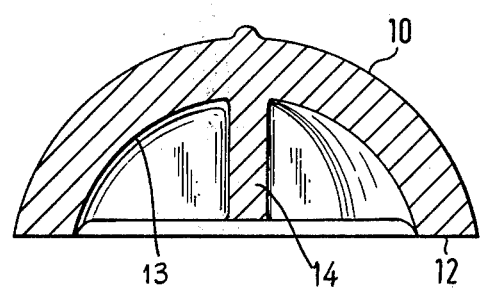
FIG. 6 is a sectional view taken along line VI—VI of FIG. 4.

The breast prosthesis per FIGS. 4-6 comprises a cup having an outer convex surface 10 and an inside concave surface 13 connected by an annular rim surface 12 facing the body of the wearer. Three stiffening ribs 14 project from the concave inside surface. The stiffening ribs 14 are recessed with respect to the rim surface 12, so that the cavity formed by the concave inside surface 13 is not subdivided into several chambers.

From the foregoing, it is seen that the devices of this invention will accomplish at least all of the stated objectives.

I claim:

1. A breast prosthesis, comprising,
   a cup portion comprised of elastic material comprising a convex outer surface, a concave inner surface, with a center, and an annular rim surface adapted to face the wearer's body,
   stiffening ribs radially extending from adjacent the center of said cup portion towards said annular rim surface,
   said annular rim surface comprising a plane,
   said stiffening ribs terminating at a position slightly removed from said plane, and
   said stiffening ribs terminating beyond said plane and outside of said cup portion.

2. The device of claim 1 wherein each of said stiffening ribs terminate before reaching the center of said cup portion.

3. The device of claim 1 wherein said cup portion is surrounded by an elastic plastic layer.

4. The device of claim 3 wherein said plastic layer is comprised of polyurethane.

* * * * *